(12) United States Patent
Zmierczak et al.

(10) Patent No.: US 8,980,196 B2
(45) Date of Patent: Mar. 17, 2015

(54) FLUID-SPARGED HELICAL CHANNEL REACTOR AND ASSOCIATED METHODS

(75) Inventors: Wlodzimierz W. Zmierczak, Salt Lake City, UT (US); Jan Dean Miller, Salt Lake City, UT (US); Raj Rajamani, Salt Lake City, UT (US); Steven Messiter, Brisbane (AU); Nicholas Drinnan, Brisbane (AU); Edward Choros, Brisbane (AU)

(73) Assignees: University of Utah Research Foundation, Salt Lake City, UT (US); Ambre Energy Limited, Brisbane (AU)

( * ) Notice: Subject to any disclaimer, the term of this patent is extended or adjusted under 35 U.S.C. 154(b) by 772 days.

(21) Appl. No.: 13/256,377

(22) PCT Filed: Mar. 15, 2010

(86) PCT No.: PCT/US2010/027335
§ 371 (c)(1),
(2), (4) Date: Feb. 13, 2012

(87) PCT Pub. No.: WO2010/105266
PCT Pub. Date: Sep. 16, 2010

(65) Prior Publication Data
US 2012/0149944 A1    Jun. 14, 2012

Related U.S. Application Data

(60) Provisional application No. 61/160,061, filed on Mar. 13, 2009.

(51) Int. Cl.
*B01J 19/24* (2006.01)
*B01J 8/22* (2006.01)
(Continued)

(52) U.S. Cl.
CPC *B01J 19/243* (2013.01); *B01J 8/22* (2013.01); *B01J 15/005* (2013.01); *B01J 16/005* (2013.01);
(Continued)

(58) Field of Classification Search
USPC .................................................. 422/228, 229
See application file for complete search history.

(56) References Cited

U.S. PATENT DOCUMENTS 4,059,419 A * 11/1977 Ross .............................. 95/214
4,165,360 A * 8/1979 Casper et al. ................. 422/202
(Continued)

FOREIGN PATENT DOCUMENTS

AU    73645/91    10/1991
EP    0475930 A1  12/1992
(Continued)

OTHER PUBLICATIONS

Lewis, catalysis (definition), Hawley's Condensed Chemical Dictionary, 1993, p. 230, 12th Edition, Van Nostrand Reinhold Company, New York.
(Continued)

*Primary Examiner* — Lessanework Seifu
(74) *Attorney, Agent, or Firm* — Thorpe North & Western, LLP

(57) ABSTRACT

A method of reacting compounds can include directing a liquid into a helical constrained flow (37) having an inner circumferential flow surface and an outer circumferential flow surface. The helical constrained flow (37) can be formed around an axial interior volume (38). At least a portion of the helical constrained flow can be exposed to a sparging portion (35) to allow a fluid to be sparged into the liquid along the helical constrained flow (37). The fluid reactant can be sparged through the helical constrained flow so as to form a fluid product.

16 Claims, 4 Drawing Sheets

(51) Int. Cl.

| | | |
|---|---|---|
| *B01J 15/00* | (2006.01) | |
| *B01J 16/00* | (2006.01) | |
| *C07C 5/05* | (2006.01) | |
| *C07C 29/154* | (2006.01) | |
| *C07C 41/09* | (2006.01) | |
| *C10G 2/00* | (2006.01) | |
| *C10G 45/00* | (2006.01) | |
| *C10G 50/00* | (2006.01) | |

(52) U.S. Cl.
CPC ............... *B01J 19/2475* (2013.01); *C07C 5/05* (2013.01); *C07C 29/154* (2013.01); *C07C 41/09* (2013.01); *C10G 2/342* (2013.01); *C10G 45/00* (2013.01); *C10G 50/00* (2013.01); *B01J 2208/00212* (2013.01); *B01J 2208/00752* (2013.01); *B01J 2219/00094* (2013.01); *C07C 2523/44* (2013.01); *C07C 2531/28* (2013.01); *C10G 2300/4081* (2013.01)
USPC ............ 422/224; 422/228; 422/229; 422/198

(56) References Cited

U.S. PATENT DOCUMENTS

| | | | |
|---|---|---|---|
| 4,714,541 A | | 12/1987 | Buyan et al. |
| 4,881,476 A | | 11/1989 | Becker et al. |
| 4,997,549 A | * | 3/1991 | Atwood ........................ 209/164 |
| 5,019,354 A | | 5/1991 | Chan |
| 5,069,885 A | | 12/1991 | Ritchie |
| 5,171,405 A | | 12/1992 | Torregrossa |
| 6,200,534 B1 | | 3/2001 | Ruottu |
| 6,521,205 B1 | | 2/2003 | Beck |
| 6,629,686 B2 | | 10/2003 | Morse et al. |
| 6,797,026 B2 | | 9/2004 | Sechrist et al. |
| 6,814,941 B1 | | 11/2004 | Naunheimer et al. |
| 6,926,749 B1 | | 8/2005 | Tenney |
| 7,066,973 B1 | | 6/2006 | Bentely |
| 7,350,962 B2 | | 4/2008 | Kao et al. |
| 7,429,621 B2 | | 9/2008 | Miller et al. |
| 7,449,155 B2 | | 11/2008 | Kao et al. |
| 2001/0021359 A1 | | 9/2001 | Johnston |
| 2009/0120850 A1 | | 5/2009 | Kruyer |
| 2009/0123349 A1 | | 5/2009 | Wu |

FOREIGN PATENT DOCUMENTS

| | | |
|---|---|---|
| JP | 5132306 | 5/1993 |
| JP | H11-116536 A | 4/1999 |
| JP | 2002-119982 A | 4/2002 |
| JP | 2008-006358 A | 1/2008 |
| WO | WO2005/090272 | 9/2005 |
| WO | WO2006/008500 | 1/2006 |
| WO | WO 2006/028873 A2 | 3/2006 |

OTHER PUBLICATIONS

PCT application PCT/US2010/027335; Mar. 15, 2010; Wlodzimierz W. Zmierczak; International Search PCT mailed Oct. 28, 2010.

* cited by examiner

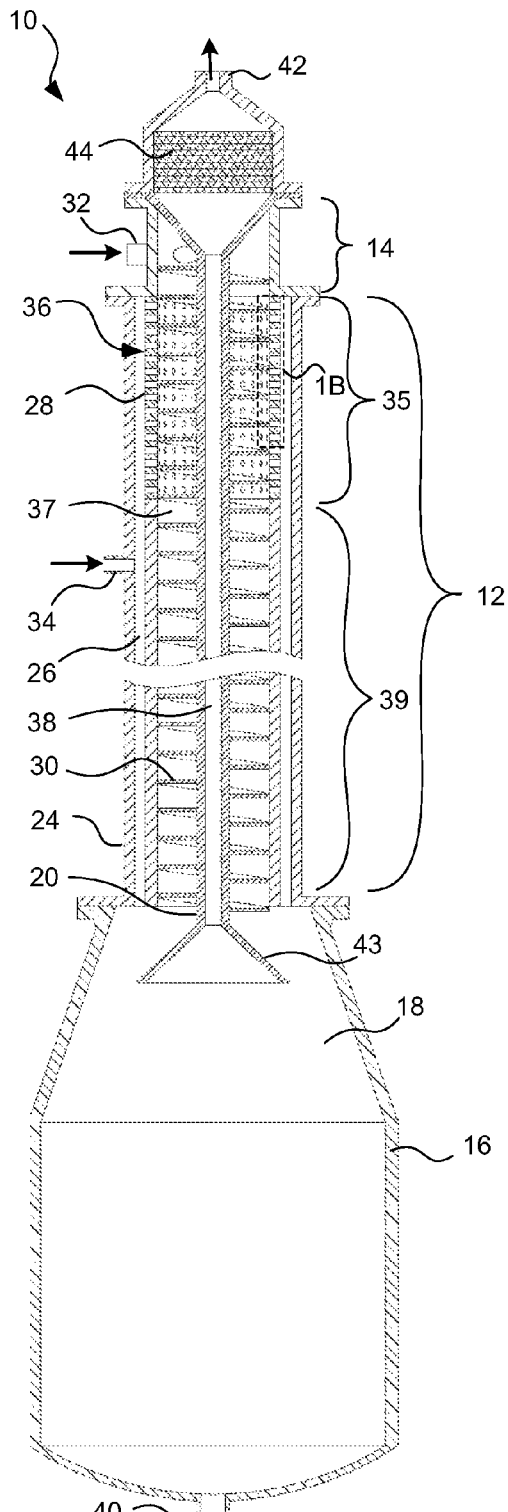
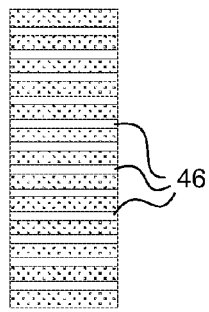
FIG. 1B
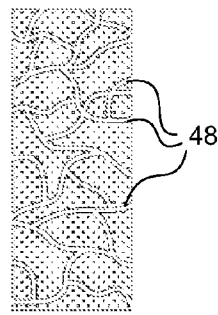
FIG. 1C
FIG. 1A

FLUID-SPARGED HELICAL CHANNEL REACTOR AND ASSOCIATED METHODS

BACKGROUND

World-wide energy consumption continues to increase at a significant rate. Many potentially useful energy sources such as nuclear, coal and some alternative energy sources are limited by governmental, societal, and/or technological barriers. As demand for energy increases, identification and development of new and suitable forms for energy storage and distribution becomes an increasingly important area of research. Hydrogen and/or some synthesis gas conversion products, e.g., methanol, higher alcohols, dimethyl ether, hydrocarbon fuels, etc., provide very promising options for replacement of most existing energy carriers. The economy of mass production of such products and chemicals depends greatly on the efficiency of processes used for their synthesis. Current options for production of these compounds are often limited by poor scalability, poor selectivity, multiple reaction and/or processing stages, and other challenges.

Therefore, devices and methods which improve selectivity and/or yields of a wide variety of synthesis processes would be a significant advancement in the area of chemical synthesis.

SUMMARY

Reactor designs that allow for improved scale-up and improved sparging would provide additional options and advantages. Particularly, improving the control over process conditions through manipulation of factors such as reactor geometry, flow dynamics characteristics, mixing effects, liquid and fluid physical properties, liquid film layer, and liquid path length, can provide additional options and advancement in the art. Accordingly, a method of reacting compounds can include directing a liquid into a helical constrained flow having an inner circumferential flow surface and an outer circumferential flow surface. The liquid can include a liquid carrier containing a catalyst, reactant, or combination of one or multiple catalysts and reactants. A fluid reactant can be sparged through the helical constrained flow from the outer circumferential flow surface to form a fluid product. The fluid product can then be removed from the reactor.

There has thus been outlined various features of the invention so that the detailed description thereof that follows may be better understood, and so that the present contribution to the art may be better appreciated. Other features and advantages of the present invention will be apparent from the following detailed description of the invention and corresponding drawings, taken with the accompanying claims, or may be learned by the practice of the invention.

BRIEF DESCRIPTION OF THE DRAWINGS

FIG. 1A is a cross-sectional view of a fluid-sparged helical channel reactor for gas feed and product applications.

FIG. 1B is an exploded side cross-sectional view of the perforated tube of FIG. 1A.

FIG. 1C is an exploded side cross-sectional view of an alternative porous tube.

Figures 2A, 2B:
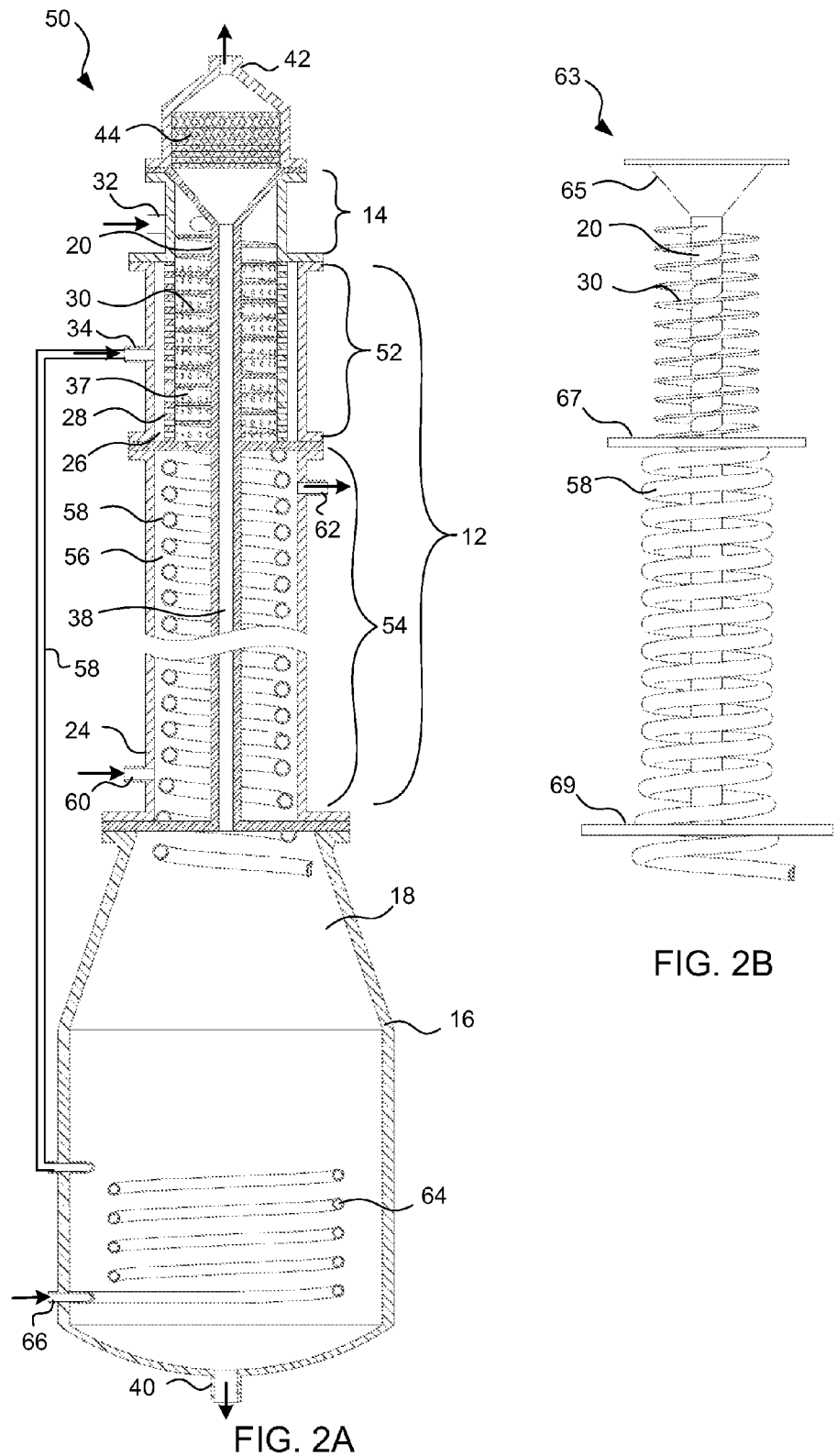
FIG. 2A is a cross-sectional view of a fluid-sparged helical channel reactor with a non-permeating coiled tube extension section for gas feed and product application.
FIG. 2B is a side view of the flat plate helical flow inducer and coiled tube extension of FIG. 2A.

The figures are provided for illustrative purposes only and are not necessarily drafted to scale. As such, variations may be had as to dimensions and proportions illustrated without departing from the scope of the present invention. Further, these drawings are illustrative of specific aspects and are not inclusive of all potential variations which fall within the scope of the invention.

DETAILED DESCRIPTION

Reference will now be made to the exemplary embodiments illustrated in the drawing, and specific language will be used herein to describe the same. It will nevertheless be understood that no limitation of the scope of the invention is thereby intended. Alterations and further modifications of the inventive features, process steps, and materials illustrated herein, and additional applications of the principles of the inventions as illustrated herein, which would occur to one skilled in the relevant art and having possession of this disclosure, are to be considered within the scope of the invention. It should also be understood that terminology employed herein is used for the purpose of describing particular embodiments only and is not intended to be limiting.

A. DEFINITIONS

In describing and claiming the present invention, the following terminology will be used.

The singular forms "a," "an," and "the" include plural referents unless the context clearly dictates otherwise. Thus, for example, reference to "a liquid inlet" includes reference to one or more of such inlets. Similarly, reference to reacting refers to one or more of such steps.

As used herein, "inner circumferential flow surface" refers to a perimetral curve defining an inner boundary of at least a portion of the helical flow path.

As used herein, "outer circumferential flow surface" refers to a perimetral curve defining an outer boundary of at least a portion of the helical flow path. Flow surfaces can be in direct contact with the helical flow, although this is not required.

As used herein, "gaseous" refers to gas phase materials which can include vapors. In particular, it is understood that gases are compounds which are in the gas phase as a result of being above their boiling point while vapors are compounds which are present in the gas phase as a vapor which is not above its respective boiling point. For example, the gaseous products can include gases, e.g. light hydrocarbons, DME, etc. and vapors, e.g. methanol, heavier hydrocarbons. Vapors can frequently be entrained within a gas, especially under vigorous mixing conditions between liquids and gases.

As used herein, "liquid" refers to liquids which are single homogeneous phase, as well as multi-phase liquids such as liquid slurry, liquid emulsions and the like (including foam and dispersions of gas in liquid).

As used herein, "fluid" refers to a material that flows in response to an applied external force. Fluids can include gases, liquids, plasmas, and can include flowable particulates or other flowable solids.

As used herein, the phrase "helical constrained flow" refers to a liquid flow path where movement of the liquid is bounded in at least two directions or planes, and where the path resembles a coil or helix. The liquid is constrained by one or more surfaces which direct the liquid along a helical path. For example, the liquid path can be constrained by at least an outer surface although a tube or other channel can be used which is formed in a helical shape.

The term "helical", "helix", and "spiral" are used interchangeably to define a liquid path in the fluid-sparged helical channel reactor. The helical path is one that winds around a central axis, similar to a spring in shape. For example, a section of flexible tubing can be used for constraining the liquid flow path. The tube can be wrapped around a cylinder such that the tube does not overlap itself, but rather wraps around in a single wrapped layer of tubing. Optional multiple passes of the helical path can be successively layered over one another. Similar configurations can be had for rectangular, contoured or other shaped conduits. Although the helical conduit which constrains flow can generally be fully enclosed, this is not always required. With respect to helical constrained flow paths, "rectangular" and "cylindrical tube" indicate the shape of the constrained flow path as a cross-section of the path taken perpendicular to the liquid flow.

As used herein, "leakage flow" refers to undesirable flow conditions where liquid in constrained flow of an outer and lower (or ramp-type) wall constraints is either flowing at a velocity that is too slow for the equipment, or too much liquid is flowing through the equipment, causing some of the liquid to leak over or run off back into the plenum or to flow into the inner volume through the inner central tube, as more fully described below.

As used herein, "sparged" or "sparging" refers to a process of dividing a fluid into multiple bodies such that surface area is increased. When sparging a fluid into a liquid, the fluid is distributed within the liquid in a two phase system such that the sparging fluid and the continuous phase liquid are maintained substantially as distinct phases, although reactions can take place at phase interfaces. Sparging can be performed between a gas and liquid, although sparging can also take place between two liquids as long as the two liquids are at least partially immiscible under the reactor conditions.

As used herein, "substantially free of" or the like refers to the lack of an identified element or agent in a composition. Particularly, elements that are identified as being "substantially free of" are either completely absent from the composition, or are included only in amounts that are small enough so as to have no measurable effect on the composition.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

B. FLUID-SPARGED HELICAL CHANNEL REACTORS

Compounds can be reacted by directing a liquid into a helical constrained flow having an inner circumferential flow surface and an outer circumferential flow surface. The liquid can contain at least one of a catalyst and a reactant. A sparging fluid can be sparged into the helical constrained flow from the outer circumferential flow surface to form a fluid product. The fluid product can be removed from the reactor for use and/or further processing.

As an illustration of a device that can be used to perform this reaction scheme, a reactor body can comprise an elongated cylindrical fluid permeating tube, an external jacket concentric with the permeating tube, and a helical flow inducer which forms a helical constrained flow within the reactor body. The permeating tube and external jacket can be spaced to form a closed gas plenum from which a sparging fluid can be sparged into liquid flowing along the helical constrained flow. An optional header can have an inlet or nozzle for feeding liquid medium into the helical flow. The liquid or slurry of solid particles suspended in a liquid medium, products and unreacted fluid, are discharged as an underflow product to a liquid container, which functions as a collection point for the liquid where products can be separated and/or recycled. The sparging fluid can be sparged through the permeating tube and sheared into numerous small bubbles or droplets by a high velocity helical flow of the liquid. Reaction is at least partially driven by the centrifugal force generated in the liquid spiral flow. Sparged disperse phase droplets move through the helically flowing liquid toward the inner surface of the helical flow path and collide with catalyst particles or contact reactant liquid moving in the opposite direction, and can undergo vigorous catalytic reaction. These transport phenomena are typically interrupted by strong turbulence of the sparged fluid in the helical channel and optional mixing coiled tube generating secondary flows which are induced by imbalance between a cross-stream pressure gradient and centrifugal forces, which induces efficient dispersion and mixing of the reactants and catalyst particles. The efficient dispersion of the reactants in the flow stream contributes to robust reaction conditions and can dramatically cut down reactor residence time. As the mixture of liquid and reaction products falls to the product collection container, the gas products can rise back through the center of an axial central tube within the helical insert to a header and an optional demister. The gas product can exit the reactor through an outlet at the top of the demister. The helical channel reactor can be used for multi-phase (gas, liquid and/or solid containing) reactions, as well as catalytic-based processes using solid or liquid catalysts.

FIG. 1A illustrates one design for a fluid-sparged helical channel reactor 10 having a helically constrained flow path. In this design, a reactor body 12 is coupled to a header 14 where liquid is injected into the reactor. The reactor body defines the helically constrained flow path in which a dominant portion of reaction occurs between the liquid and a sparged fluid contained in the flow stream. The sparged fluid can be a gas but can optionally be another fluid, e.g. liquid. An integrated liquid container 16 can be oriented at an end of the reactor body opposite the header so as to collect liquids and gases as they flow from the reactor body. An open space 18 can allow gases and liquids to separate from one another. Gaseous fluids can generally be collected via a central tube 20 back up through the reactor body. However, gases can also be directly withdrawn from the liquid container such that the axial space or central chamber 38 within the helical flow is either blocked, void space, used for circulation of cooling fluids or the like. Liquids can be collected in the liquid container and removed via a suitable liquid outlet 40. Each of these aspects is described in more detail below along with additional optional features.

The reactor body 12 can include a cylindrical constrained flow unit located within a reactor shell 24 to form a plenum chamber 26 between the reactor shell and the constrained flow unit. The constrained flow unit can include an elongated cylindrical fluid permeating tube 28, an inner central tube 20 oriented within the fluid permeating tube, and a helical flat plate 30 oriented between the fluid permeating tube and the central tube. These three elements are configured to define a helical constrained flow. The helical constrained flow forces fluids to travel spirally downward in a helical flow defined by the surfaces of the constrained-flow unit. Generally, each of the reactor body and the constrained-flow units are cylindrical; however, the reactor body can have alternative contours or shapes which do not adversely affect the helical constrained flow pattern. For example, an expanding conical porous tube can be used to keep the flow linear as the fluid is sparged into the helical constrained flow, e.g. increasing total volumetric flow. The reactor body can generally be a cylindrical body, although other shapes can be used which do not interfere with the functions described herein.

A liquid inlet 32 can be fluidly connected to the reactor body 12 and configured to allow addition of a liquid into the helical constrained flow path. This can be located at any suitable location; however, in one aspect the liquid inlet is oriented within the header 14 at an upper end of the reactor body. Further, the liquid inlet can be tangentially oriented to direct the liquid into the constrained helical flow path. This tangential orientation can be beneficial in directing the incoming liquid into the helical path. In embodiments using liquid slurries at a high space velocity, a tangential injection can reduce wall erosion within the header. The liquid can be any suitable liquid which can act as a carrier for a catalyst or can participate in the reaction. The liquid can be inert with respect to the reaction, can include a reactant, or can itself be a reactant. The liquid can contain suspended solids including, but not limited to, particulate catalysts, solid particulate reactants, and/or nanoparticles. Non-limiting examples of liquids can include oil (i.e. a mixture of similar molecular weight compounds of the same type) carriers, ionic liquids, reactant liquids, single pure chemical carrier, and the like. In one aspect, the liquid includes an oil carrier. In one aspect, the oil carrier can be a high boiling carrier which remains liquid under conditions within the reactor. In another aspect, the liquid can be a chemical carrier (e.g. decalin, methanol, water, and the like). Other liquid carriers can include, but are not limited to, mineral oils such as paraffin oils, silicone oils, heavy fractions of the petroleum product, liquid reactant, and mixtures of these materials. In one aspect, the liquid can be an ionic liquid, which is generally defined as a salt composed solely of a cation and an anion that melts at temperatures of below 100° C. Functionalization can tune their physical and chemical properties and generate an unlimited number of liquids acting as acids, bases or ligands. Non-limiting examples of ionic liquid cations include 1-alkyl-3-methylimidazolium, 1-alkyl-2,3-dimethylimidazolium, 1-alkyl-3-alkylimidazolium, N-alkylpyridinium, 4-methyl, N-alkylpyridinium, N-alkyl, N-methylpyrrolidinium, tetraalkylphosphonium, and tetraalkylammonium. Typically, the anions are inorganic and include $[PF_6]^-$, $[BF_4]^-$, $[AlCl_4]^-$, $[CF_3SO_3]^-$, $[(CF_3SO_2)_2N]^-$, although some organic anions (e.g. $[RCO_2]^-$) also can be introduced. Ionic liquids can be particularly useful to keep catalyst particles suspended during helical constrained flow, collection, and recycling. Ionic liquid properties make them highly efficient media and catalysts for bi-phasic or tri-phasic reactions between fluid reactants. In the reactor, the ionic liquids can be use as liquid carriers, liquid carriers/catalysts, liquid carriers/solvents, or liquid carriers/catalysts/solvents. Ionic liquids can also be useful to suspend and stabilize metal nanoparticles, e.g., Pd nanoparticles embedded in 1-n-butyl-3-methylimidazolium hexafluorophosphate or tetrafluoroborate, which remain suspended during helical flow, collection, and recycling. In such case ionic liquids can participate in formation and stabilization of catalytically active transition metal nanoparticles and other catalyst nanoparticles. Optionally, the liquid may also contain one or more liquid reactants. Non-limiting examples of liquid reactants include water, organic compounds subjected to hydrogenation, alkylation, etc. Those skilled in the art can choose suitable liquids based on the desired chemical reaction, viscosities, operating temperature, potential reactions with reactants or other species, ease of separation, and the like.

A sparging fluid can be directed into the reactor for reaction with the liquid. The fluid is sparged into the helical constrained flow. The fluid can be a gas such that the gas is sparged into a liquid, although sparging of a liquid into another liquid can be viable as long as the sparging fluid is at least partially immiscible in the helically flowing liquid. In the turbulent constrained flow, proficient dispersion of the bubbles can cause intensive contact with liquid reactant and/or catalyst particles. Therefore, the gas bubbles undergo extensive reaction. In one alternative, the sparging fluid can be miscible with the helically flowing liquid. In this case, the sparged fluid intimately mixes with the helical liquid to form a single phase liquid in helical flow.

As an illustration of potential conditions, numerous small bubbles/droplets sparged and sheared from the reactor porous surface by the flow stream, generally tend to move toward the inner surface of the channel while solid catalyst particles tend to move toward the external surface of the channel. However, usually, this tendency is at least partially overshadowed by the turbulent flow phenomena generated in a liquid/slurry flowing through the helical channel or a coiled tube at a constant angular velocity. In such a flow, secondary flows are generated which are induced by imbalance between a cross-stream pressure gradient and centrifugal forces. Further, the pitch between the coil segments enables the imposition of a torsion effect. These secondary flows form a variety of vortices rotating in different directions which result in liquid flow turbulences causing rapid chaotic movement of the bubbles/droplets resulting in intensive contact with other reactants and/or the liquid catalyst or solid catalyst particles and promoting catalytic reaction at short residence times.

The sparging fluid can be a gaseous reactant with optional carrier gases. The fluid can comprise a single gaseous reactant or a plurality of gaseous reactants, along with optional inert carriers. Specific composition of the fluid can largely depend on the type of reaction being performed within the reactor. However, a few non-limiting examples of such fluids can include synthesis gas, hydrogen, carbon monoxide, oxygen, and carriers can include nitrogen, helium, and other non-reactive gases, and combinations thereof.

A plenum chamber can be useful to deliver the sparging fluid to the helically flowing liquid. A fluid feed such as plenum inlet 34 can be fluidly connected to the reactor body 12 for supply of a sparging fluid to the plenum chamber 26. The plenum chamber can have any suitable shape or volume. However, as a general rule the volume merely needs to be sufficient to provide fluid which can be effectively transported into the helical constrained flow. The fluid permeating tube 28 defines an inner wall 36 of the plenum chamber and can have a sparging portion 35 which distributes fluid into the helical constrained flow 37. In one specific aspect, sparging can include forcing the sparging fluid across a wall configured to sparge the fluid. As such the fluid permeating tube includes openings which allow passage of fluid across the tube wall. These openings can include, but are not limited to, perforations (e.g. cylindrical), slits, mesh, permeable membrane, fits, and the like. Generally, the outer circumferential flow surface of the fluid permeating tube can be composed of any material capable of increasing surface area of the gas for contact with the liquid. Specific non-limiting examples of suitable materials include porous walls or tubes, mesh, grating, asymmetric static mixers, and the like. Porous walls or tubes can be produced of metal (e.g. stainless steel), Hastelloy C®, Inconel®, ceramic, plastic fits, as well as stainless steel mesh or perforated tubes. In another alternative aspect, the fluid permeating tube can be a gas separating membrane such as, but not limited to, non-porous polymeric or ceramic membranes, metal membranes (e.g. palladium membrane which permits only hydrogen), ion conducting membranes, and the like. Optionally, an external surface of the gas separating membrane can contain a catalyst which generates gas which can be transported through the membrane (e.g., catalytic reformers generating hydrogen).

Optionally, the fluid permeating tube can also include a catalyst material secured to the tube such that sparging fluid contacts the embedded catalyst as it passes through the inner wall. The catalyst material can be placed between two porous walls (e.g. perforated walls, mesh screen, or the like). Alternatively, the catalyst material can be embedded or otherwise attached to the wall, i.e. such that the porous wall acts as a catalyst support. For example, the catalyst material can be deposited or coated onto the wall surfaces.

FIG. 1B is an enlarged view of a portion of a perforated wall of the fluid permeating tube showing a plurality of perforations 46. FIG. 1C shows a porous material forming the fluid permeating tube having random meandering paths 48 through which sparging fluid can be passed. Each opening type can have benefits and drawbacks for particular applications, e.g. ease of manufacture and suitability. For example, fits can tend to clog when used with slurries but can be very effective for gases and solid free liquids. The particular configuration of openings can be a function of the desired sparged surface area, flow rates, fluid composition, etc. For example, in some aspects the residence time in the reactor body is a matter of seconds or, in many cases, less. As such, a high flow rate is needed from the plenum chamber across the fluid permeating tube. Some permeable membranes would not be suitable for such a design while perforated tubes would be desirable. Alternatively, when lower flow rates are used, a low pore size permeable membrane or similar material can be suitable (e.g. ceramic or polymeric such as PDMS and the like). Smaller pore sizes can also allow for smaller sparged fluid bubble size and increased dispersion of sparging fluid. Typical perforations can range from about 0.1 mm to about 0.3 mm for certain applications, although larger or smaller openings can also be suitable. For example, smaller pore sizes in porous frit or membranes can fall well below 0.1 mm such as 0.01 mm to about 0.1 mm and are only limited by available material pore sizes.

The fluid permeating tube can also optionally have a non-sparging portion 39 which allows at least a portion of the helical flow to react without incoming sparging fluid. Further, the plenum inlet can be oriented in a region of the plenum chamber where there are substantially fewer or no openings at the fluid permeable tube, e.g. in the non-sparging portion 39 of the fluid permeating tube 28. This can reduce channeling of fluid at that region. Therefore, the fluid permeating tube can have one or more selected regions or openings along its length, e.g. an upper region and/or a lower region, or multiple sparging regions, e.g. a first sparging region and a second sparging region separated by a non-sparging region. In a variation of this multiple region aspect, multiple plenum chambers can be optionally provided in series along the fluid permeating tube to allow a serially staged sparging by different sparging fluids. This can allow for changes in sparging fluid composition and/or concentration, for example. Such staged sparging can also allow for multi-staged reactions to be performed in a common reactor body.

Regardless of the specific sparging configuration, as sparging fluid enters the constrained-flow unit, it is sparged (e.g. increased surface area) as it crosses the fluid permeating tube 28 into the helical constrained flow. The helical constrained flow can be formed by a suitable wall or walls to form a substantially enclosed helical flow path (i.e. including inlets and outlets). The flow path can be constructed from concentric tubes and a helical flat plate bridging the annular space as described in connection with FIG. 1A. Alternatively, the helical constrained flow can be formed by a coiled tube. The helical flow path can be configured to have a rectangular cross-section, circular cross-section or any other suitable channel cross-section. For example, the helical flow can be formed generally by a helical flow inducer such as the flat plate helix 30. Other materials can also be used which guide flow along a helical flow path. For example, the helical flow inducer can be formed using a helical U-shaped channel, a helical three-sided wall channel, or other shapes which contribute to guiding a helical flow.

The constrained flow path spirals at least one full rotation in a helix, although the number of passes or rotations can vary considerably and depend on the designed residence time and materials. In one aspect, the number of helical rotations can be from about five to about one hundred, and in one aspect can be from about ten to about thirty rotations, although almost any number of rotations can be suitable depending on the application. The helical flow path spirals around the central column or tube. In this configuration, the outer surface of the central tube acts as an inner circumferential flow surface. Further, the inner circumferential flow surface need not always be in direct contact with the helical flow. At least a portion of the helical flow path also passes the sparging portion of the permeating tube. Incoming sparged fluid can be immiscible with the bulk liquid of the helical constrained flow (e.g. this is a heterogeneous reaction). This outer circumferential flow surface can be defined by the permeating tube or a corresponding non-sparging portion of the tube. Typically, each of the rotations of the helical flow path is equal in circumference and incline angle, and can be evenly spaced, although this is not required. The helix can be varied in any suitable configuration, such as tighter or closer-together spirals near the liquid inlet. Alternatively, the helix can be generally conical such that toward the lower end of the helical flow, the helical flow path becomes tighter, e.g. having a smaller curvature diameter and/or increased inclination.

The helical constrained flow allows high shear mixing of the fluid with the liquid and subsequent reaction between components of the fluids. It should be kept in mind that the flow rates of fluids along the reactor body within the constrained helical flow are typically very high such that both gases and liquids travel downward through the reactor body, e.g. a few seconds or less residence time. As these fluids flow through the flow unit, gaseous products or carriers tend to migrate towards the inner tube 20. The central inner tube can optionally include openings (not shown) sufficient to allow excess gases to escape from the helical constrained flow and into the central chamber 38 of the inner tube. Such openings can be perforations (e.g. cylindrical), slits or other openings which allow excess gases to escape, while also restraining the liquid within the helical constrained flow. Some loss of liquid via leakage flow into the central chamber is generally acceptable and in some cases can be less than about 1%, depending on the reaction design. In one aspect, the inner tube does not have openings such that gases exit the lower portion of the helical path into the liquid container 16. Gases which enter the central chamber travel upward such that the central chamber is part of or connected to the gas outlet 42 for removal of gas products.

The helical flat plate 30 is optionally removable from at least one of the fluid permeating tube (FPT) 28 and the inner central tube 20. This can facilitate removal for cleaning, replacement, and/or other maintenance. In one option, the helical flat plate is permanently attached to the inner tube as a single replaceable unit as discussed in connection with FIG. 2B and FIG. 3B. The FPT and the helical flat plate can be designed so that they can be removed either from the top or from the bottom. Such a design can reduce or eliminate load on the FPT from other components of the reactor. An alternative option is to attach the FPT to the outer edge of the helical flat plate permanently. Thus, the helical flat plate can be permanently attached to the inner tube, permanently attached to the FPT, or can be easily separable from one or both the inner tube and FPT. The inner tube can be made of a solid tube, a fluid permeable tube or a tube with narrow slots to separate gaseous products from the liquid. During operation the enclosed helical flow path can be substantially filled or can be only partially filled with liquid/gas mixture. The helical flow path can be defined by an upper helical ceiling and a lower helical floor. It is noted that successive passes of the helical flow path allow the upper and lower helical walls (i.e. the helical flat plate) to act simultaneously as a floor and a ceiling for successive passes.

In one optional aspect, the helical constrained flow can be in the form of a cylindrical tube that is coiled in a generally circular geometry, or in a rectangular-shaped tube that is coiled in a generally helical geometry. A rectangular-shaped tube geometry may be in the form of one integrated piece with a shared outer circumferential flow surface. The integrated piece may also have a shared inner circumferential flow surface and a helical track connecting the outer circumferential flow surface and the inner circumferential flow surface.

Although the outlet and inlet positions for sparging fluids and the primary helical liquid in the reactor system can be placed so that the liquid enters near the top of the reactor and exits near the bottom, and the sparging fluid enters near the middle to bottom of the system and is removed through the top, this particular arrangement is not required. Optionally, the reactors can include multiple inlets and/or outlets for the permeating fluid and/or liquid. Multiple inlets can allow for staged reactions, charging of depleted reactants, and/or augmentation of fluid flows. Alternatively, there can be two separate liquid constrained flow paths, e.g., forming a double-helix arrangement or a set of concentric helical flow conduits. Such an arrangement can provide a compact design to minimize reactor space and can also allow for manipulation of heat transfer and/or side reactions. Furthermore, two separate liquids can be used wherein one constrained flow path is designed such that the gas sparges through both liquids separately, i.e. the gas first travels through a distance of one liquid and then passes into the second constrained flow path and through the second liquid. Thus, the two helical paths are concentric to one another. In this manner sequential reactions can be performed consecutively in the same reactor unit. For example, a multi-stage reaction gas be performed where the gaseous product of the first flow path can be immediately directed (e.g. via a common intermediate porous wall) to a second constrained flow path having a different liquid reactant and/or catalyst for production of a final gas product. Such multiple flow paths can be oriented in a co-current or counter-current arrangement.

An optional floating inner tube can be oriented concentrically within the permeating tube. This can allow for automatic adjustment of the separation point depending on the flow rate of liquid through the reactor. The buoyancy of the floating inner tube (not shown) can be designed to allow the bottom portion to define the respective gas and liquid flow rates into each portion of a separation unit oriented below the reactor body 12. In one aspect, the floating inner tube can be the axial central tube 20.

A liquid outlet 40 can be fluidly connected to the reactor body for removal of liquid and/or slurry from the reactor body. In the embodiment shown in FIG. 1A, the liquid container 16 is oriented intermediately between the reactor body 12 and the liquid outlet. The liquid container can generally have a volume sufficient to allow at least a portion of entrained gases to separate from the liquid in upper open space 18 and escape into the gas outlet 42 via the inner chamber 38. The central tube 20 can include a flared inlet opening 43 which can allow initial separation of liquids from gases before contact with the opening upon exit from the helical flow path 37. Optionally, the liquid container can be operated under reduced pressure (e.g. ambient pressure) to increase gas-liquid separation within the liquid container. The bottom of the liquid container can optionally be contoured to reduce accumulation or settling of solids. The liquid container can collect and optionally cool liquid and reaction products. Further, foam which comes out of the reactor body can be sprayed into the liquid container to allow foam to separate into liquid and the gas disengages from the liquid. Alternatively, this separation can be accomplished using a cyclone, impact surface, or spraying using a nozzle or the like. Collected liquids can be removed, stored and/or recycled. Depending on the reaction and the specific liquid, this may be done on a continuous basis for an extensive period of time and cycles. Depending on the state of the liquid after exiting the reactor system, the collected liquid may need re-conditioning, testing, filtering or re-charging (in the case of some catalysts), prior to recycling. Re-conditioning can include recharging the catalyst, altering the composition, and/or changing the temperature of the stream. Once the removed liquid is in a suitable condition, the liquid may be inserted into the system once again into the helical constrained flow.

In one alternative, the constrained flow spirals and can then enter a final reaction zone prior to collection in the liquid container. This final reaction zone or mixing zone can add length to the reaction path that allows continuation of the reaction, further separation of the gas and liquid phases, and cooling of the liquid. The reactor can further include an optional separation unit fluidly connected between the constrained flow spiral coil and the liquid and gaseous product outlets or liquid container. The separation unit may have a non-spiraled coil section where further reaction can occur. This can be accomplished by a path that takes the reaction slurry through an optional open cyclone portion between the helical and/or coiled tube and the collection vessel. This configuration is designed such that gas produced during the extra length of reaction path can then naturally rise into the central column and exit with the rest of the gaseous product. The last length of reaction path can have a section of cooling coils wherein cooling fluid flows so as to reduce the temperature of the liquid sufficient to allow reuse.

The gas outlet 42 can be fluidly associated with an upper end of the reactor body 12 for removal of gaseous products or excess gas by-products. Sparging often creates a foamed slurry of gas and froth, depending on the particular reaction system. As such, froth can enter the gaseous product stream which can produce a mist. The gaseous stream can enter a froth trap oriented within the reactor wherein the liquid froth is separated from the gaseous product. The gases can then be removed in a final gas stream, and the liquid from the mist and/or froth can be recycled into the reactor. Accordingly, an optional demister 44 can be fluidly connected within the header 14 between the gas outlet and the inner chamber 38. The demister can be any device which removes entrained liquid or vapor from the outlet fluid stream by coalescence of mist into larger droplets which can be allowed to flow downwardly through the inner chamber and separate from the gas/vapor stream. Non-limiting examples of suitable demisters can include wire mesh, vaned packing, structured packing, pads, fixed baffles, other impingement separators, and the like. Care can be taken to choose demisters which do not create excessive back pressure, especially with high space velocity applications.

The reactor can be optionally configured to operate at high pressures. As such, high pressure materials (e.g. of sufficient gauge and design) can be used for the reactor shell 24, liquid container 16, header 14, and associated high pressure seals at junctions. Furthermore, high pressure pumps can be used to force liquid and/or fluid into the respective inlets in order to control the flow rates and associated internal pressures. High pressure controllers and/or back pressure regulators can also be used to deal with the associated high pressures throughout the system. High pressures can vary but can be from about 5 bar to about 300 bar. Some reactions require predetermined pressure ranges to be maintained, while others can merely benefit from the reduced residence times and improved interfacial contact between reactants and/or catalysts. In some applications, a high space velocity is desirable such that residence times can be less than a few seconds, and in some cases less than a second. Although conditions can vary dramatically depending on the particular reactions desired, a high space velocity from about 1 liter/sec to about 1000 liter/sec can be readily achieved with correspondingly high yields and/or efficiencies.

FIG. 2A illustrates a fluid-sparged helical channel reactor 50 which is designed for production of dimethyl ether (DME) and other products from synthesis gas (syngas). This same configuration can also be suitable for other reactions and processes as well, especially those which are highly exothermic and/or involve solid catalysts. Without repeating much of the same discussion as for FIG. 1A, we note that similar or the same features are identified using the same reference numbers and most of the same principles apply to this configuration.

In FIG. 2A, a catalyst slurry is introduced at slurry inlet 32 and a syngas can be introduced at plenum inlet 34. The liquid container 16 thus holds catalyst slurry and any other liquid products. The reactor body 12 can include a sparged helical section 52 which operates as previously described with a gas plenum 26 which leads to a fluid permeating tube 28. Incoming fluid is sparged through the permeating tube into the helical constrained flow path 37. The helical flow path is defined by the helical flat plate 30, the fluid permeating tube, and inner axial tube 20.

The reactor body 12 can further include a mixing section 54 which can be used for temperature control and further mixing. In this mixing section, the reactor shell 24 can define a chamber 56 within which a coiled tube 58 is placed. The chamber can have a cooling fluid inlet 60 and a cooling fluid outlet 62. A heat transfer fluid can be passed through the chamber via the inlet and outlet so as to remove excess heat from the liquid flowing along the helical path. This can be particularly desirable for highly exothermic reactions such as DME production and other such exothermic reactions. The mixing section can thus be used as a cooling mantle and/or merely provide additional mixing and residence time for further reaction.

However, cooling elements can be present in any step of the removal, including the separation step and/or can be inserted into the inner column of the reactor body. In one aspect, the reactor can have cooling elements placed within the reactor (i.e. within the inner column, plenum, separation or collection vessel, or the like). Alternatively, a cooling element can be oriented against outer surfaces of the reactor body to remove excess heat from the reactor.

FIG. 2B shows the helical portion of the reactor body removed as an integrated helical insert 63. This insert can include the parts together as shown or can be optionally segmented further using threaded engagements, pin-slots, detents, or other locking mechanisms to secure parts together. For example, in one option, the top portion of the helical channel can be removed separately from the mixing portion. Regardless, the insert shows an upper conical gas outlet 65 which simultaneously serves as the lower floor of the demister unit and the upper ceiling of the fluid entry within the header. The axial central tube 20 has the helical flat plate 30 wrapped around the outer tube surface such that the flat plate width is generally transverse the axis of the central tube. An intermediate flange 67 creates a fluid barrier between the sparging section and the cooling mantle. The coiled mixing tube 58 is wound about the central tube such that the helical flow path is generally continued from the upper sparging section. A lower flange 69 forms a fluid barrier between the cooling mantle and the liquid container. The coiled tube can optionally extend beyond the lower flange partially into the liquid container. Although not required, the coiled tube can have an outlet which directs fluids (i.e. gases, liquids, and slurry) tangentially into an inner wall of the liquid container.

Figures 3A, 3B:
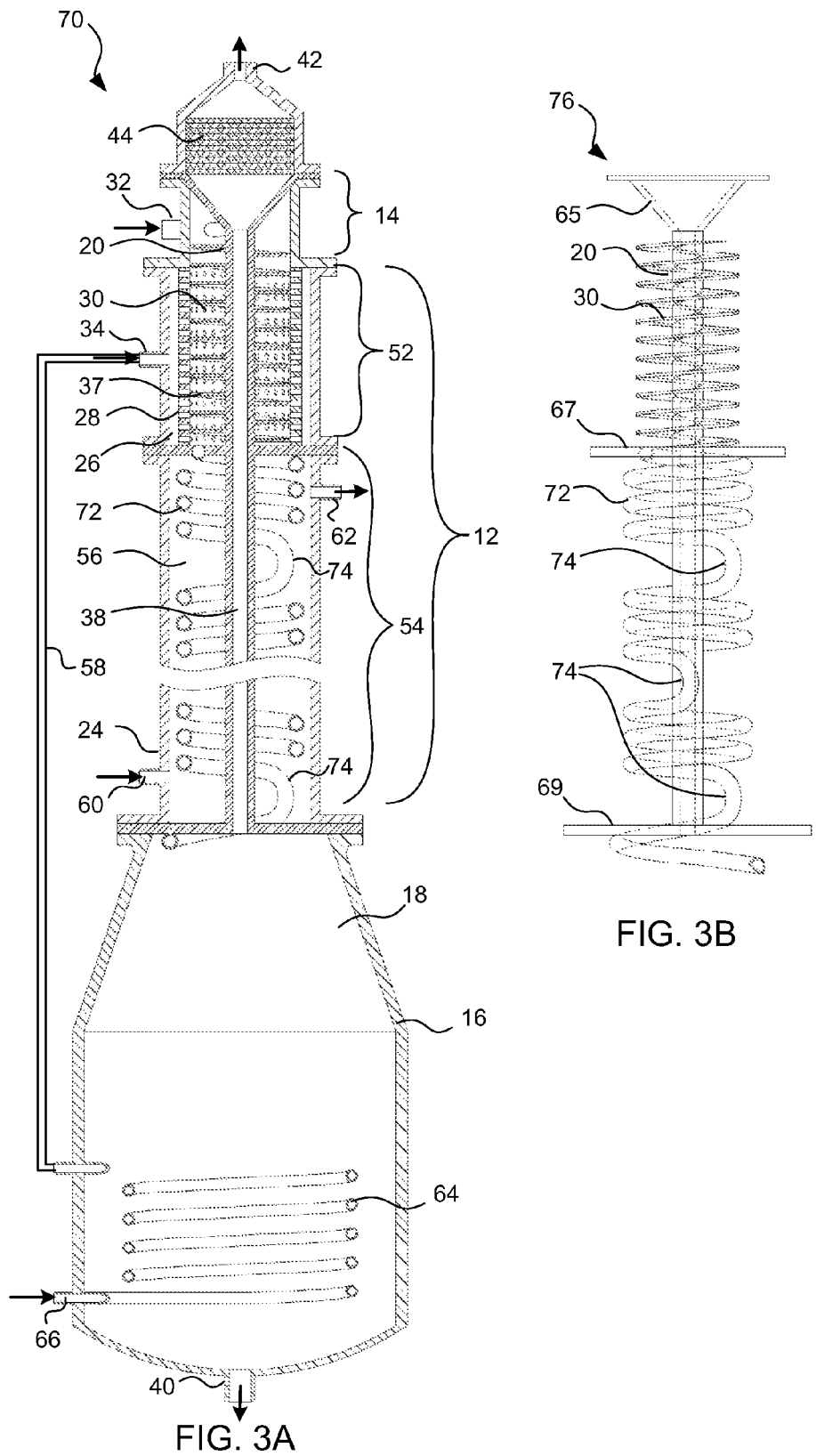
FIG. 3A is a cross-sectional view of a fluid-sparged helical channel reactor with alternating (clockwise and counter-clockwise) rotation direction in the coiled tube extension for gas feed and product application.
FIG. 3B is a side view of the flat plate helical flow inducer and coiled tube extension of FIG. 3A having an alternating direction coiled tube configuration.

FIG. 3A presents another optional configuration for a sparged helical channel reactor 70. This configuration is similar to that shown in FIG. 2A, except the mixing portion 54 has an alternating clockwise and counter-clockwise helical rotation of the coiled tube 72. More specifically, the coiled tube can have a first section of coiled passes which follows the direction of the helical path of the sparging portion 52 followed by one or more bends 74 in the coil which reverse the coil direction between clockwise and counter-clockwise. FIG. 3B shows the helical portion of the reactor body removed as a helical insert 76. As mentioned previously, the insert can be configured to be removable for cleaning and/or maintenance. The alternating rotation of the mixing coils can in some cases further enhance mixing. For example, with a continuous coil, gases and/or particulates can trend towards inner or outer portions of the tube, respectively. Alternating the rotation direction can encourage movement of the gases and/or particulates away from such surfaces and prevent excessive concentrations at the inner or outer circumferential surfaces. It is emphasized that such migration is at least partially interrupted by the substantial turbulence and multiple sub-vortices which exist within helical turbulent flow. Regardless, alternating coil direction can further enhance mixing and contact between the solid particulates, gases, and liquids which are present in the helical flow.

A gas-liquid separator (e.g. cyclone not shown) can be optionally oriented between the reactor body 12 and the catalyst slurry container 16. The gas-liquid separator can provide additional space, and under some conditions additional reaction time, for gases and liquids to separate and flow towards the central chamber 38 and liquid container, respectively. A slurry composed of solid catalyst particles (e.g. average size of less than 20 µm) suspended in a high-boiling liquid (e.g., paraffin oil) can be discharged as an underflow product to the slurry container which functions as a collection point for the liquid where a reaction or another process is quenched and reaction products separated.

Preheating elements 64 can optionally be thermally associated with the interior volume and configured for transferring heat from the liquid to feed fluids during reactions. The preheating elements are shown as a coiled tube oriented within the liquid container 16. Alternatively, the preheating elements can be oriented outside of the liquid container but in thermal contact therewith to allow heat to be transferred from the liquid container to the syngas or other fluids prior to introduction into the helical flow path. Optional cooling elements can also be wrapped around the outside walls of the container, within the container, or any other location suitable to remove heat from the collected liquids. Thus, the syngas (or other reaction fluid) can be introduced at preheater inlet 66 and pass through the preheater and then be directed to the plenum inlet 34 via a inlet line 58.

Figure 4:
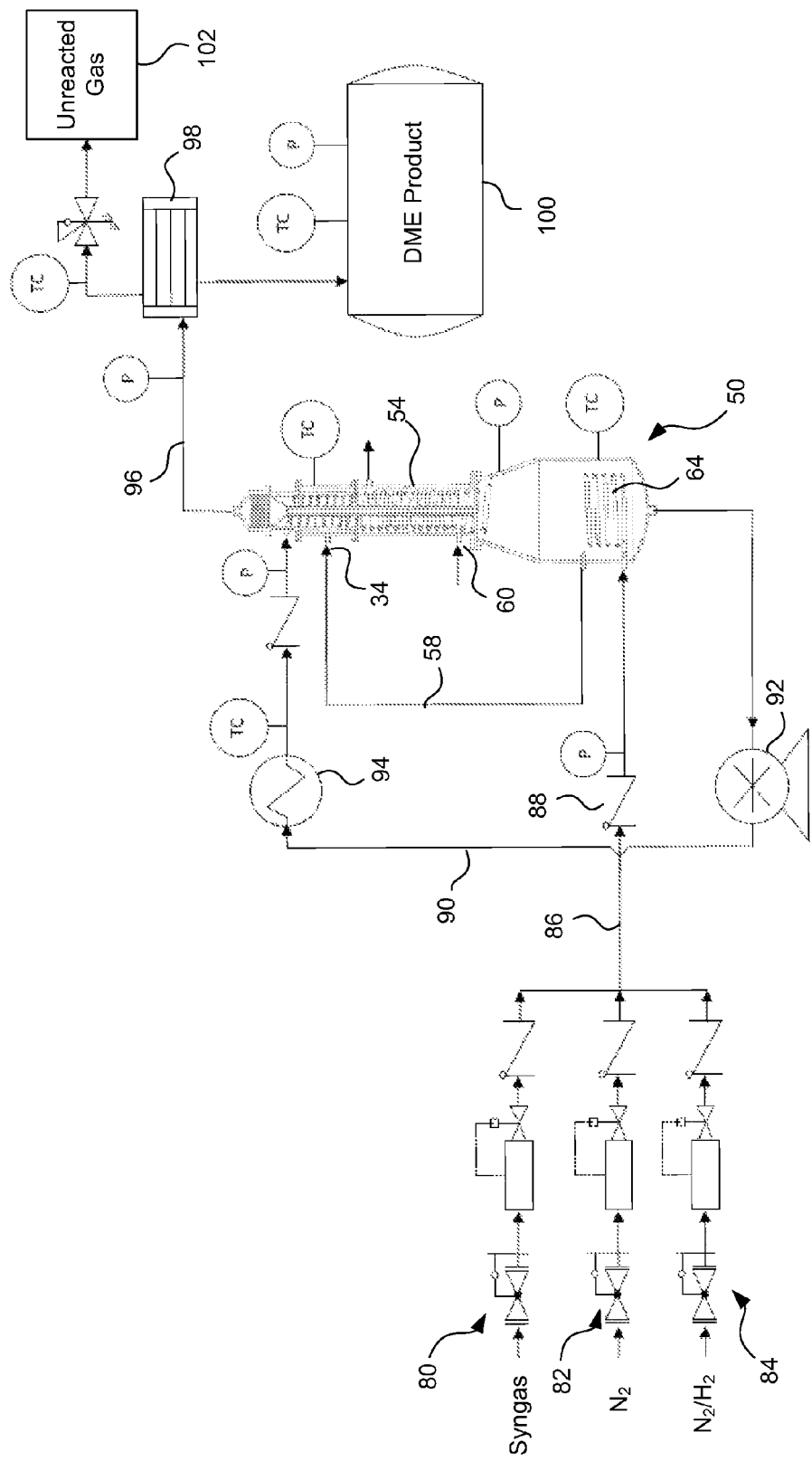
FIG. 4 is a piping and instrumentation diagram (P&ID) of a helical channel reactor (HCR) system designed for conversion of synthesis gas to dimethyl ether (DME).

FIG. 4 shows a process flow for DME production from syngas. A mixture of syngas, nitrogen, and/or helium-hydrogen can be selectively controlled in relative proportions using respective valve assemblies 80, 82, and 84 (including solenoid flow control, inlet valves and cut-off valves). Outlets from each of these gas sources can be combined into a single supply line 86 which is directed to the reactor 50 via optional control cut-off valve 88. In this case, the syngas mixture is preheated in preheater 64 and then routed via line 58 to fluid inlet 34. An optional cooling fluid can be direct through the cooling mantle 54 via coolant inlet 60. Catalytic slurry liquids are recycled via recycle line 90 from the reactor back to header inlet 32. A pump 92 and heater 94 can optionally be used to control inlet conditions of flow rate and temperature. Gas products can be withdrawn from the reactor via gas product line 96 and sent to a heat exchanger 98 where DME product is condensed and delivered to a product vessel 100. Unreacted gases represented by unit 102 can be either recycled, stored, used as fuel, or utilized for other purposes.

In another alternative aspect, catalyst can be optionally activated in a pretreatment step. This pretreatment can be performed before introduction into the reactor and optionally in an integrated step within the liquid container 16. A catalyst pretreatment agent or its precursor can be injected into the catalyst slurry to begin activation. Alternatively, the agent or its precursor can be injected into the reactor body such that activation occurs within the constrained flow. The catalyst pretreatment can be performed by gradual increase of temperature from ambient to desired temperature. The heating rate should be insufficient to cause substantial agglomeration of catalyst particles or formation of less catalytically active oxidative states. Further, heating rate and hydrogen content can be regulated to prevent or substantially reduce hydrogen in exit gases. As a general guideline, the heating rate can be about 0.2° C./min to about 10° C./min such as about 0.5° C./min or 1° C./min. In one example, the inactive catalyst can be pretreated in an activation step by heating from ambient to about 230°-240° C. over about 16 hours. The mixture can be held at this temperature for about 6 hours to finalize activation, although other hold times can be suitable. Catalyst pretreatment can involve circulation through a reactor bypass loop via a pump, external or internal preheater.

In practice, the liquid and fluid can then be introduced into the reactor body as discussed previously. This can be done at the high temperature involved in catalyst activation. Alternatively, the reactor and liquid container can be cooled to room temperature. In this case, the fluid or syngas can be introduced as the temperature is ramped up to the desired reaction temperature while the catalyst slurry is cycled through the reactor. In one case, the ramp time can be about 30 minutes, although other times can be suitable depending on the particular compositions and conditions.

A fluid-sparged helical channel reactor can provide excellent dispersion of gaseous reactants with a catalyst slurry, high throughput per unit reactor volume, short residence time, small consumption of catalysts, and superior mass and heat transfer characteristics. The catalytic helical channel reactor can be particularly suitable for strongly exothermic catalytic slurry syngas-to-liquid fuels processes, such as direct DME production. However, a broad range of other applications can be accommodated. The helical channel reactor has many advantages such as excellent dispersion of the gas and liquid, which ensures, among other things, robust reaction conditions, reduced consumption of any catalyst and, in some cases, suppression of unwanted side reactions. Due to the outstanding mass and heat transfer characteristics, and high throughput per unit reactor volume, use of this reactor can enable significant reduction in capital and operational costs of syngas processes. Additionally, the helical channel reactor has many advantages and can be readily sized and scaled up. The helical channel reactor allows for greater control over the liquid layer thickness, liquid path, liquid velocity, and selection of liquid for use in the system.

In a fluid-sparged helical channel reactor, a gas composition can be forced through a porous material designed to sparge and increase the surface area of the sparging fluid. Through use of the fluid-sparged helical channel reactor (HCR) the flow rate of the liquid can be easily adjusted to achieve a predetermined liquid layer thickness. Using an HCR, the layer thickness can range upwards of about 0.5 to about 20 inches or greater depending on the reactor design. As a result, the sparging fluid is forced to travel through a substantially greater length of liquid, and allowing for greater variability of reaction conditions, process efficiency, and capacity to use materials that may not completely react in cyclone-type reactors. Due to the strong turbulence, the liquid in the helical constrained flow can improve collision efficiency between smaller gaseous bubbles and the liquid reactants, suspended reactants, and/or suspended catalyst.

A wide range of chemical synthesis processes can be carried out using the reactors and associated methods described herein. Several examples of classes or reactions which are suitable for use include, but are not limited to, synthesis of methanol, dimethyl ether, Fischer-Tropsch reaction hydrocarbon products, higher alcohols, oxidation products, alkylation products, oligomerization products, hydrogenation products, and hydrotreated hydrocarbons. Several of these types of reactions are described below in more detail.

Specific operating conditions can vary, depending on the desired reaction. However, the helical channel reactor can typically operate at reaction temperatures in the range of −20-450° C. and pressure range of 1-300 bar. However, the reactor can operate over a wide range of temperature and pressure outside these ranges. The materials and thickness of the reactor body and elements can be adjusted in order to accommodate high reaction temperatures and pressures. For example, the thickness of the reactor body can be increased or decreased to account for varying reactor conditions (i.e. temperature, pressure). The reactor body can be formed of any material which is non-reactive with the liquid and gas compositions and is capable of withstanding the operating conditions such as temperature, pressure, abrasiveness and the like. Non-limiting examples of suitable materials includes stainless steel, Hastelloy C®, Inconel® (Ni—Cr—Fe alloys), ceramic, and plastics. Furthermore, the length, number of rotations, direction of rotation, distance between constraining flow surfaces, and dimensions can be varied to optimize the reactor for specific reactions.

In the case of highly exothermic reactions (syngas processes e.g. DME synthesis, alkylation, etc.), the process temperature can be determined either by controlled temperature of liquid and reaction substrates, vaporization of lower boiling liquid products into the gas phase, and/or insertion of a cooling coil into the interior volume of the reactor. Generally, cooling elements can be placed in thermal contact with the interior volume of the reactor. Alternatively or additionally, cooling elements may be placed in contact with the helical constrained flow, e.g. cooling mantle.

Practical Applications

The fluid-sparged helical channel reactors can be used in a wide variety of chemical synthesis processes. By way of one example, the chemical reaction can be a catalytic reaction. Additionally, the reaction can be any chemical reaction with liquid, gas, or suspended reactants, or any combination thereof. In the case of a catalytic reaction, a catalyst can be provided as part of the liquid carrier to form a solid-liquid catalyst slurry (unless using a liquid catalyst). Reactions of this type are multi-phase reactions which include a solid catalyst, liquid carrier, reaction products and a gaseous reactant. In some embodiments, the catalytic reactions are reactions involving at least three phases.

Suitable processes can include, but are not limited to, syngas processes (e.g. methanol, dimethyl ether, Fischer-Tropsch, and higher alcohols syntheses); partial oxidation of organic compounds; hydrocarbon conversions (e.g. alkylation, olefin oligomerization, hydroprocessing of heavy oils, bio-oils, tar sand oils, coal-derived liquids and shale oil); and other processes with gas, liquids, and/or solids slurries, or processes with gases and two liquid phases. The liquid carrier can be any high-boiling fluid capable of establishing the desired flow in the helical constrained flow path, and in some cases, capable of suspending catalyst particles therein.

The examples outlined below are not to be taken as an extensive or complete listing of applicable processes. Rather, the examples below outline applications of various embodiments of the method and device presented herein.

Synthesis gas or "syngas" (typically a mixture of $H_2$, CO and $CO_2$, although other gases can be present), can be sparged through the porous outer circumferential flow surface into the helical flow path, and sheared by the catalyst-in-oil-slurry flow stream into numerous small bubbles, e.g. often in the range of 50 to 500 micrometers. This results in an outstanding dispersion of syngas feed and excellent contact of the syngas with the catalyst. The design of the helical constrained flow allows settings wherein the distance the gas must travel is greatly variable and may be set at greater than about three inches thick.

By way of example, methanol can be produced from syngas using catalysts such as Cu/ZnO, Cu/ZnO/$Al_2O_3$, Cu/ZnO/MnO, Raney Cu—Al—Zn, Raney Cu—$Al_2O_3$, ThCu$_x$, and ZrCu$_x$. Typical reaction conditions for methanol synthesis are temperatures from about 180° C. to about 350° C. and pressures from about 20 bar to about 150 bar. Non-limiting examples of suitable liquids carriers include mineral oils such as fully saturated paraffin oils (e.g., $C_{12}$-$C_{20}$), waxes, decalins (including alkylated decalins), and the like.

In another example, dimethyl ether can be produced from syngas using catalysts such as co-catalyst systems composed of methanol synthesis catalysts (see above), mostly Cu—ZnO—$Al_2O_3$, and dehydration catalysts (e.g., zeolites such as HZSM-5, alumina, and aluminum phosphate). Typical reaction conditions for dimethyl ether synthesis are temperatures from about 220° C. to about 280° C. and pressures from about 30 bar to about 70 bar. Liquid carriers such as those described previously can similarly be used.

In yet another process example, various hydrocarbons can be produced via Fischer-Tropsch processes. In order to produce lower alkanes ($C_2$-$C_4$), catalysts such as Fe/K, Fe/Mn, Fe/Mn/Ce, Fe/K/S, Ru/$TiO_2$, Fe/C, Mo/C, and the like can be used. Gasolines can be produced using catalyst such as fused Fe/K, Co/$ThO_2$/$Al_2O_3$/silicalite, Fe/K/ZSM-5, Co-ZSM-5, Ru-ZSM-5, Ru/ZSMi-5, FeCu/K-ZSM-5, and the like. Diesel fuels can be formed using catalysts such as Fe/K, Ru/V/$TiO_2$, Co/Zr, Ti/$Al_2O_3$, Cr/$Al_2O_3$, Co/Zr/$TiO_2$, Co—Ru/$Al_2O_3$, and the like. Heavier waxes can be formed using catalysts such as Fe/Cu/K, Fe/Ru, Co/Zr, Ti/$Al_2O_3$ or Cr/$Al_2O_3$. Typical reaction conditions for Fischer-Tropsch synthesis are temperatures from about 180° C. to about 350° C. and pressures from about 20 bar to about 50 bar. Non-limiting examples of suitable liquid carriers include paraffin oils (e.g., $C_{12}$-$C_{20}$), heavy oil Fischer-Tropsch products, and the like.

Higher alcohols can be synthesized from syngas using catalysts such as sulfided Mo-based catalysts (K/$MoS_2$, Cs—$MoS_2$, K—Co—$MoS_2$, Ni—K—$MoS_2$, Ni—Mn—K—$MoS_2$), unsulfided Mo-based catalysts (K—$CO_1Mo_x$, K—Co-β-$Mo_2$C), modified methanol synthesis catalysts (K—ZnO—$Cr_2O_3$, K—Cu—ZnO—$Cr_2O_3$, Cs—Cu—ZnO—$Cr_2O_3$, Cs—Cu—ZnO—$Al_2O_3$), noble metals-based catalysts (Rh/$Al_2O_3$, Rh—Mn—$SiO_2$, Rh—Mo/$ZrO_2$, Rh/$ZrO_2$), modified Fischer-Tropsch catalysts (Co, Fe, Ni, and Ru metal supported on $SiO_2$ or $Al_2O_3$ with promoters such as Cu, K, etc.), and. homogeneous catalysts (Co, Ru, and Rh metal complexes and bimetallic complexes). Typical reaction conditions for higher alcohol synthesis are temperatures from about 200° C. to about 425° C. and pressures from about 10 bar to about 200 bar. Non-limiting examples of suitable liquid carriers include mineral oils such as fully saturated paraffin oils (e.g., $C_{12}$-$C_{20}$), and the like.

Partial oxidation of organic compounds can also be a useful reaction. A mixture of $O_2$ (or air), optionally with a hydrocarbon reactant, can be used for the oxidation of a variety of organic compounds. Non-limiting examples of suitable liquid carriers include paraffin oils (e.g., $C_{12}$-$C_{20}$), water, liquid reactant, and the like. When using water as a liquid carrier, typically lower temperatures are desirable in order to reduce decomposition and/or deactivation of the catalyst material. Oxidations reactions such as, but not limited to, methanol to formaldehyde using high purity silver powder or $Fe_2O_3$/$Cr_2O_3$/$MoO_3$ catalysts, ethylene to ethylene oxide using $Ag/\alpha$-$Al_2O_3$ catalyst, propylene to acrolein/acrylic acid using $BiO_2$/$Mo_2O_3$ catalyst, ammoxidation of propylene to acrylonitrile using $Bi_2O_3$—$MoO_3$/$SiO_2$ catalyst, n-butane to maleic anhydride using vanadium-phosphorus-containing (VPO) or VPO/$TiO_2$ catalysts, and ethylene to vinyl acetate using $Pd/SiO_2$ or $PdCl_2$/$CuCl_2$ catalysts.

The following hydrocarbon conversion processes represents a broad variety of possible synthesis reactions which are suitable. Aliphatic alkylation with solid catalysts can be accomplished using a solid acid catalyst suspended in a liquid carrier and fed into the reactor. Non-limiting examples of suitable liquid carriers include fully saturated paraffin oils (e.g., $C_{12}$-$C_{20}$) and the like. Gaseous reactants, such as olefins and isobutane, are sparged through the outer circumferential flow surface and sheared into numerous small bubbles by the helical liquid flow. Potential solid acid catalysts for this process are exchanged zeolites, ion-exchange resins (e.g., AMBERLYST and NAFION), superacid solids (e.g., chlorinated alumina and sulfated zirconia), immobilized superacids (e.g., HF—$SbF_5$/$Al_2O_3$, $BF_3$/zeolites or oxides or resins), ionic liquid Lewis acids, and heteropolyacid-based catalysts.

Olefin oligomerization can be accomplished using a solid catalyst suspended in a liquid carrier. The solid catalyst suspended in a liquid carrier can be fed into the helical constrained flow of the reactor and gaseous olefins are sparged through the sparging portion and sheared into numerous small bubbles by the helical liquid flow. Non-limiting examples of suitable liquid carriers include paraffin oils (e.g., $C_{12}$-$C_{20}$), liquid reactants, and the like. Phosphoric acid on a solid support (e.g., quartz and kieselguhr) or amorphous or crystallizes (zeolites) silica-aluminas can be a suitable catalyst.

Hydrogenation reactions can also be advantageously pursued. For example, $H_2$ as a reducing agent can be sparged through the gas-sparging device and sheared into numerous small bubbles by the high-velocity swirl flow of the liquid carrier, where it can undergo reaction catalyzed by a catalyst contained within the liquid carrier. Non-limiting examples of suitable liquid carriers include paraffin oils (e.g., $C_{12}$-$C_{20}$), liquid hydrogenation products (e.g., recycled products), and the like. Suitable catalysts can include precious metals such as Pd, Pt, Rh, and Ru unsupported and supported (e.g., Pt/C, Pd/$Al_2O_3$), and Ni, Cu, Cr and Co and their oxides (e.g., Raney Ni, Ni/$Al_2O_3$, and CuO—$Cr_2O_3$). An example of a hydrogenation reaction is the hydrogenation of gaseous olefins to paraffins using Raney Ni as a catalyst.

Hydrocracking, like catalytic cracking is commonly used to convert refinery heavy cuts to lighter products, e.g., propane, butane, naphtha, kerosene, etc. For example, a liquid carrier such as vacuum distillate, deasphalted residues, gas oil, kerosene, etc., can be fed to the reactor together with suspended finely divided catalyst particles. Hydrogen can be used as the reactant gas that is sparged through the porous outer circumferential flow surface. Suitable hydrocracking catalysts can include, but are not limited to, CoMo/$SiO_2$—$Al_2O_3$, NiW/$SiO_2$—$Al_2O_3$, CoMo/$Al_2O_3$ (acid treated), NiW/$Al_2O_3$ (acid treated), Pt/zeolite, and Pd/zeolite. An example of a hydrocracking reaction is the hydrocracking of vacuum distillate to naphtha at temperature of 380° C., pressure of 100 bar using Pd/Y-zeolite catalyst.

Further, most conventional hydrotreating reactions in the petroleum refining industry can be accomplished in these fluid-sparged helical channel reactor systems. For example, heavy oil, or any petroleum derived oil as well as tar sand, bitumen, shale oil, coal liquids or bio-oils, that needs to be upgraded can be fed to the reactor as the liquid carrier, together with suspended finely divided catalyst particles. Hydrogen can be used as the reactant gas that is sparged through the porous tube in order to effect such reactions as hydrodesulfurization, hydrodenitrogenation, hydrodeoxygenation, hydrocracking, and the like. Although a wide variety of catalysts can be suitable, NiMo/$Al_2O_3$, NiW/$Al_2O_3$, and CoMo/$Al_2O_3$ are most common. Other reactions can include refining and/or treatment of heavy petroleum residues, bio-oils, tar sands, coal-derived liquids and shale oil.

EXAMPLE 1

A direct process for production of dimethyl ether (DME) includes synthesis of methanol and its dehydration to DME, which are performed at the same time in the same reactor. Since the DME synthesis reaction is highly exothermic, the slurry helical channel reactor system demonstrated in FIG. 4 can be effectively employed to assure a high syngas conversion and excellent process heat transfer management.

To perform a reaction run, the sample of catalytic slurry containing 20 wt % of a bifunctional catalyst containing 95 wt % of CuO—ZnO—$Al_2O_3$ methanol synthesis catalyst and 5 wt % of H-ZSM-5 methanol dehydration catalyst in the form of fine particles (1 to 10 μm in size) suspended in an inert paraffin oil, Penreco® Drakeol® 34, is introduced to the slurry container (50). The reactor system is purged with nitrogen flow through gas preheater (64) and reactor gas inlet (34). To initiate the catalyst pre-reduction, the pump (92) starts circulation of the slurry through the helical reactor, and heat exchanger (90) starts the heat-up period of the catalytic slurry and nitrogen flow is replaced with the flow of 4% $H_2$+96% $N_2$ catalyst pre-reduction mixture. Catalytic slurry flow rate is established at the level needed to achieve an average linear speed of the slurry in the helical channel of about 4 m/sec. In situ catalyst reduction is performed under ambient pressure according to the following heating program: heating from room temperature to 260° C. at a rate of 0.5° C./min and kept at peak temperature for 8 h. After this pre-treatment, the $H_2$/$N_2$ mixture flow is replaced with the flow of DME reaction feed syngas ($H_2$/CO=1) and the reactor is pressurized to 50 bar (reactor pressure). Syngas flow rate depends of the reactor size and diameter of perforations in the gas permeable tube (28). Temperature of the reaction mixture (catalytic slurry and reacting gases and products) is maintained, using steam flow as a cooling agent, within a range of 260 to 265° C. Reactor products leave through the top reactor outlet (42) to a condenser (98) where DME and methanol vapors are separated from unreacted syngas and directed to the liquid product tank.

EXAMPLE 2

Stable palladium nanoparticles embedded in 1-n-butyl-3-methylimidazolium hexafluorophosphate can catalyze bi-phasic hydrogenation of olefins at a temperature of 20 to 100° C. The slurry helical channel reactor system presented in FIG. 4, after some modifications of the reactor system including use of different gases and elimination of the product cooling function, can be effectively employed to assure excellent mixing and distribution of hydrogen in the catalytic liquid.

To perform a reaction run, the sample of Pd nanoparticles embedded in 1-n-butyl-3-methylimidazolium hexafluorophosphate is introduced to the slurry container (50). The reactor system is purged with nitrogen flow through gas preheater (64) and reactor gas inlet (34). The pump (92) starts circulation of the ionic liquid through the helical reactor and heat exchanger (90) heats-up quickly the catalytic liquid to 75° C. and then nitrogen flow is replaced with the flow of hydrogen and 1,3-butadiene under ambient pressure. Catalytic liquid flow rate is established at the level needed to assure the linear speed of the slurry in the helical channel equal to 4 m/sec. Reactor products leaving the reactor through the top reactor outlet (42) to the condenser (98) where unreacted butadiene and butene products are separated from hydrogen and directed to the liquid product tank. The condensed 1,3-butadiene and butenes mixture can be subjected to separation in a column.

Thus, there is disclosed an improved reactor and methods for preparing chemical compounds. The above description and examples are intended only to illustrate certain embodiments of this invention. It will be readily understood by those skilled in the art that the present invention is susceptible to a broad utility and applications. Many embodiments and adaptations of the present invention other than those herein described, as well as many variations, modifications and equivalent arrangements will be apparent from or reasonably suggested by the foregoing description thereof without departing from the substance or scope of the present invention. The foregoing disclosure is not intended or to be construed to limit the present invention or otherwise to exclude any such other embodiment, adaptations, variations, modifications and equivalent arrangements, the present invention being limited only by the claims appended hereto and the equivalents thereof.

What is claimed is:

1. A fluid-sparged helical channel reactor, comprising:
   a) a constrained-flow unit located within a reactor body, said unit having an inner wall and an outer wall configured to produce a helical constrained flow along a substantially enclosed helical flow path around an axial interior volume, wherein at least part of the outer wall includes a sparging portion to allow fluid reactant to be sparged into the helical constrained flow;
   b) a liquid inlet fluidly connected to the reactor body and configured to allow addition of a liquid into the enclosed helical flow path;
   c) a sparging fluid inlet fluidly connected to the reactor body for supply of a sparging fluid to the sparging portion of the constrained-flow unit;
   d) a liquid outlet fluidly connected to the reactor body to allow removal of liquid from the constrained-flow unit;
   e) a gas outlet fluidly associated with the enclosed helical flow path to allow removal of gases from the enclosed helical flow path;
   f) a separation unit fluidly connected between the helical flow path and the liquid outlet and gas outlet, said separation unit allowing at least partial separation of gases and liquids; and
   g) a gas preheater, separate or operatively coupled to provide sparging fluid to the sparging fluid inlet and thermally associated with the separation unit such that the sparging fluid is heated by heat transferred from the separation unit before introduction into the sparging fluid inlet.

2. The fluid-sparged helical channel reactor of claim 1, further comprising a plenum chamber oriented between the sparging fluid inlet and the constrained-flow unit to allow distribution of the sparging fluid into the sparging portion.

3. The fluid-sparged helical channel reactor of claim 1, further comprising a cooling mantle thermally associated with the reactor body and configured for removing heat from the liquid during exothermic reactions.

4. The fluid-sparged helical channel reactor of claim 1, wherein the sparging portion is at least one of a porous mass or a perforated wall.

5. The fluid-sparged helical channel reactor of claim 1, further comprising a demister fluidly connected to the gas outlet.

6. The fluid-sparged helical channel reactor of claim 1, wherein the helical constrained flow unit further comprises a helical mixing section oriented downstream of the sparging portion.

7. The fluid-sparged helical channel reactor of claim 6, wherein the helical mixing section includes at least one alternating clockwise and counter-clockwise helical rotation.

8. The fluid-sparged helical channel reactor of claim 1, wherein the gas outlet is fluidly connected to the axial interior volume such that gases can be withdrawn up through the axial interior volume.

9. A fluid-sparged helical channel reactor, comprising:
   a) a constrained-flow unit located within a reactor body, said unit having an inner wall and an outer wall configured to produce a helical constrained flow along a substantially enclosed helical flow path around an axial interior volume, wherein at least part of the outer wall includes a sparging portion to allow fluid reactant to be sparged into the helical constrained flow and the constrained-flow unit includes a helical mixing section oriented downstream of the sparging portion and the helical mixing section includes at least one alternating clockwise and counter-clockwise helical rotations;
   b) a liquid inlet fluidly connected to the reactor body and configured to allow addition of a liquid into the enclosed helical flow path;
   c) a sparging fluid inlet fluidly connected to the reactor body for supply of a sparging fluid to the sparging portion of the constrained-flow unit;
   d) a liquid outlet fluidly connected to the reactor body to allow removal of liquid from the constrained-flow unit; and
   e) a gas outlet fluidly associated with the enclosed helical flow path to allow removal of gases from the enclosed helical flow path.

10. The fluid-sparged helical channel reactor of claim 9, further comprising a plenum chamber oriented between the sparging fluid inlet and the constrained-flow unit to allow distribution of the sparging fluid into the sparging portion.

11. The fluid-sparged helical channel reactor of claim 9, further comprising a cooling mantle thermally associated with the reactor body and configured for removing heat from the liquid during exothermic reactions.

12. The fluid-sparged helical channel reactor of claim 9, wherein the sparging portion is at least one of a porous material and a perforated wall.

13. The fluid-sparged helical channel reactor of claim 9, further comprising a separation unit fluidly connected between the helical flow path and the liquid outlet and gas outlet, said separation unit allowing at least partial separation of gases and liquids.

14. The fluid-sparged helical channel reactor of claim 13, further comprising a gas preheater operatively coupled to provide sparging fluid to the sparging fluid inlet and thermally associated with the separation unit such that the sparging fluid is heated by heat transferred from the separation unit before introduction into the sparging fluid inlet.

15. The fluid-sparged helical channel reactor of claim 9, further comprising a demister fluidly connected to the gas outlet.

16. The fluid-sparged helical channel reactor of claim 9, wherein the gas outlet is fluidly connected to the axial interior volume such that gases can be withdrawn up through the axial interior volume.

* * * * *